(12) United States Patent
Podsiadlo

(10) Patent No.: US 9,790,458 B2
(45) Date of Patent: Oct. 17, 2017

(54) TUBE-IN-TUBE BUBBLE COLUMN PHOTOBIOREACTOR

(71) Applicant: ExxonMobil Research and Engineering Company, Annandale, NJ (US)

(72) Inventor: Paul Podsiadlo, Easton, PA (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 0 days.

(21) Appl. No.: 15/138,447

(22) Filed: Apr. 26, 2016

(65) Prior Publication Data

US 2016/0326475 A1 Nov. 10, 2016

Related U.S. Application Data

(60) Provisional application No. 62/156,393, filed on May 4, 2015.

(51) Int. Cl.
*A01G 33/00* (2006.01)
*C12M 1/00* (2006.01)
*C12M 1/12* (2006.01)
*C12M 1/02* (2006.01)
*A01G 7/02* (2006.01)
*A01G 7/04* (2006.01)
*A01G 31/00* (2006.01)
*C12N 1/12* (2006.01)

(52) U.S. Cl.
CPC .............. *C12M 21/02* (2013.01); *A01G 7/02* (2013.01); *A01G 7/045* (2013.01); *A01G 31/00* (2013.01); *A01G 33/00* (2013.01); *C12M 23/06* (2013.01); *C12M 23/20* (2013.01); *C12M 23/22* (2013.01); *C12M 23/34* (2013.01); *C12M 25/00* (2013.01); *C12M 31/02* (2013.01); *C12M 31/08* (2013.01); *C12M 41/10* (2013.01); *C12M 41/22* (2013.01); *C12N 1/12* (2013.01)

(58) Field of Classification Search
CPC .............................. A01G 33/00; C12M 21/02
See application file for complete search history.

(56) References Cited

U.S. PATENT DOCUMENTS 5,958,761 A 9/1999 Yogev et al.

FOREIGN PATENT DOCUMENTS

WO 2008033573 A2 3/2008

OTHER PUBLICATIONS

Database WPI Week 199914, abstract, Thomson Scientific, Nov. 18, 1998, London GB.
PCT/US2016/029322 International Search Report and Written Opinion dated Apr. 26, 2016.

*Primary Examiner* — Rosanne Kosson
(74) *Attorney, Agent, or Firm* — Amanda K. Jenkins

(57) ABSTRACT

Systems and methods are provided for growing algae and/or other microorganisms in a controlled environment while reducing or minimizing the amount of energy required for maintaining desired conditions in the growth medium. The systems can be based on a photobioreactor having a "tube-in-tube structure", where an outer cylindrical tube contains a heat regulation fluid that surrounds one or more inner cylinders that contain microorganisms in growth media. The heat regulation fluid in the outer cylinder, as well as the outer cylinder itself, can assist with regulating the temperature of the growth media in the inner cylinder(s).

11 Claims, 12 Drawing Sheets

US 9,790,458 B2

TUBE-IN-TUBE BUBBLE COLUMN PHOTOBIOREACTOR

CROSS-REFERENCE TO RELATED APPLICATIONS

This application claims the benefit of provisional U.S. Ser. No. 62/156,393, filed May 4, 2015, the entire contents of which are expressly incorporated by reference herein.

FIELD OF THE INVENTION

This invention relates to systems and methods for growing photosynthetic microorganisms such as algae in a photobioreactor environment.

BACKGROUND OF THE INVENTION

Developing renewable sources of feedstocks based on biomass for making distillate products, such as fuels or lubricants, is an area of ongoing interest. Use of biomass as a feedstock source is attractive from a perspective of avoiding depletion of mineral oil and gas sources. However, a variety of challenges remain in developing technologies for harvesting and processing feeds derived from biomass.

One potential source of biomass-derived feedstocks includes algae. Algae are an advantageous form of biomass in part because algae growth environments can be constructed, such as photobioreactors or artificially constructed ponds. Such photobioreactors and/or algae growth ponds can be placed in desirable locations, such as locations that do not compete with production of food for human consumption.

U.S. Pat. No. 5,958,761 describes a photobioreactor that includes a tubular housing surrounding an inner tubular growth environment. A fluid can be pumped through the tubular housing to provide control for the temperature in the photobioreactor.

SUMMARY OF THE INVENTION

In an aspect, a method for growing microorganisms is provided. The method can include providing a first cylinder having a first volume containing a heat regulation fluid, a diameter of the first cylinder being about 15 cm to about 120 cm, the first cylinder having a surface comprising a coating, the coated surface having an average transmittance for wavelengths between about 400 nm and about 700 nm of at least about 0.6 and an average transmittance for wavelengths between about 950 nm and about 1100 nm of about 0.5 or less; providing a second cylinder having a second volume containing a growth media comprising micro-organisms, the second cylinder being contained within the first cylinder, a longest axis of the second cylinder being substantially parallel to a longest axis of the first cylinder, a diameter of the second cylinder being about 3 cm to about 25 cm, a ratio of a surface area of the first cylinder to a surface area of the second cylinder being at least about 4, for example at least about 8 or at least about 12; exposing the cylinder to a light source comprising visible radiation and infrared radiation to grow the micro-organisms; and maintaining an average temperature of the growth media within the second cylinder of about 0° C. to about 60° C. during a characteristic time period.

In another aspect, a system for growing microorganisms is provided. The system can include a first cylinder having a first volume, a diameter of the first cylinder being about 15 cm to about 120 cm, the first cylinder having a surface comprising a coating, the coated surface having an average transmittance for wavelengths between about 400 nm and about 700 nm of at least about 0.6 and an average transmittance for wavelengths between about 950 nm and about 1100 nm of about 0.5 or less; a second cylinder having a second volume, the second cylinder being contained within the first cylinder, a long axis of the second cylinder being substantially parallel to a long axis of the first cylinder, a diameter of the second cylinder being about 3 cm to about 25 cm, a ratio of a surface area of the first cylinder to a surface area of the second cylinder being at least about 4, for example at least about 8 or at least about 12; a first cylinder inlet and a first cylinder outlet in fluid communication with the first volume; and a second cylinder inlet and a second cylinder outlet in fluid communication with the second volume and not in fluid communication with the first volume.

DETAILED DESCRIPTION OF THE EMBODIMENTS

Figure 1:
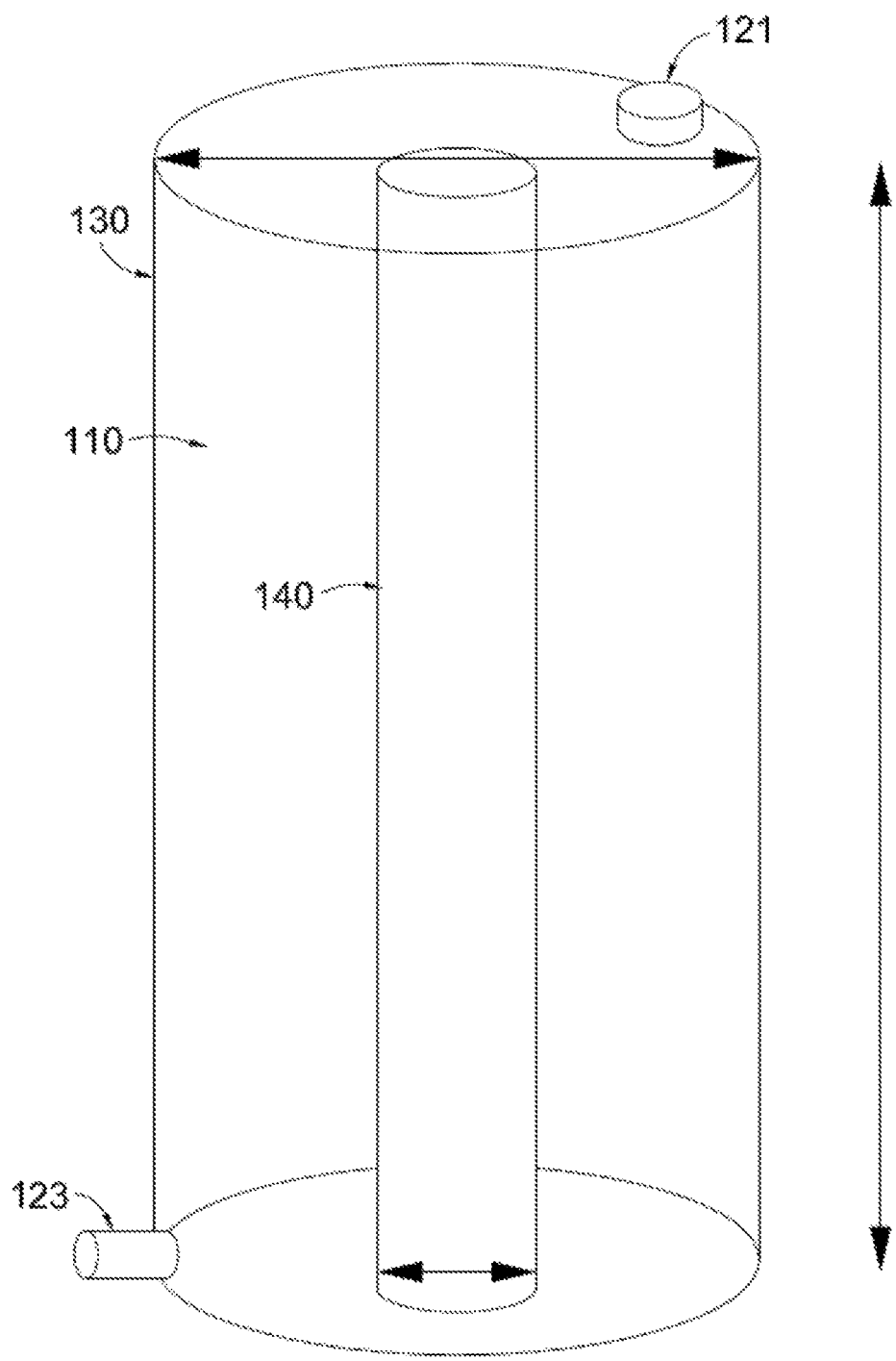
FIG. 1 schematically shows an example of a configuration for a tube-in-tube photobioreactor.

In various aspects, systems and methods are provided for growing algae and/or other (particularly photosynthetic) microorganisms in a controlled environment while reducing and/or minimizing the amount of energy required for maintaining desired conditions in the growth medium. The systems can be based on a photobioreactor having a "tube-in-tube structure", where an outer cylindrical tube contains a heat regulation fluid surrounding one or more inner cylinders that contain micro-organisms in growth media. The heat regulation fluid in the outer cylinder, as well as the outer cylinder itself, can assist with regulating the temperature of the growth media in the inner cylinder(s).

In some aspects, the regulation of the conditions in an inner cylinder can occur without the use of additional equipment (e.g., mechanical means) for movement of the heat regulation fluid, such as pumps. Instead, the temperature in the inner cylinder can be regulated based on the amount of heat regulation fluid in the outer cylinder and/or by use of a reflective coating, such as on the outer surface of the outer cylinder. The reflective surface can allow a majority of radiation in the visible range to be transmitted through the coating and into the inner cylinder(s) while reflecting a majority of infrared radiation.

Closed photobioreactors can be beneficial relative to open ponds or photobioreactors based on improved control over the algae growth environment. In conventional photobioreactors, one of the difficulties in using a closed system can be managing the temperature in the reactor environment. Typical sources of visible light, such as sunlight, also usually serve as sources of infrared light. Although infrared light typically does not contribute to photosynthesis by algae, infrared light can be absorbed by water. As a result, the aqueous media typically used as a growth medium for algae can be heated due to absorbed infrared radiation. Depending on the location of a photobioreactor and the time of year, absorption of infrared light can lead to substantial temperature swings. Substantial temperature swings can substantially reduce the growth rate of algae within a photobioreactor.

One way of mitigating temperature fluctuations due to infrared radiation can be to include a barrier layer of water and/or another infrared absorbing medium in a photobioreactor. The barrier water can then be circulated or otherwise moved in order to replace barrier water that is at an elevated (or lower) temperature with water at a more desirable temperature. While this can be an effective strategy, it can have a drawback related to energy usage of artificial water circulation/movement. Due in part to the multiple steps required for conversion of algae into a fuel product, seemingly small energy losses during growth and/or harvesting of algae can dramatically impact the overall energy production/profitability. As a result, active management of temperature in a photobioreactor by circulation of a separate barrier layer of water can significantly reduce the net energy generated from growth and harvesting of algae for fuel production.

In various aspects, instead of mechanically circulating an external layer of fluid for temperature regulation, a passive method of heat regulation can be used. An external reflective layer can be used to reduce and/or minimize the amount of infrared radiation absorbed by water and/or another heat regulation fluid. By controlling the amount of infrared radiation absorbed, a desirable level of temperature control can be achieved by using a sufficient amount of the heat regulation fluid relative to the size of the volume for growing micro-organisms.

Passive regulation of temperature can also allow for other advantages in the tube-in-tube photobioreactor configuration. Because a reduced and/or minimized amount of water circulation can be necessary, the photobioreactor can more easily be oriented as a vertical column. This can allow the photobioreactor to receive sunlight effectively without having to modify the orientation of the photobioreactor to match the relative position of the sun.

Tube-in-Tube Structure

In various aspects, temperature regulation for a closed photobioreactor system can be provided using an outer cylinder that contains an inner cylinder (or optionally a plurality of inner cylinders). Temperature regulation can be achieved in part by having a sufficient volume of a heat regulation medium in the outer cylinder.

The outer cylinder can have any convenient shape, although a right circular cylinder can be advantageous for providing an isotropic surrounding environment for a cylinder in the interior. In this discussion, the outer cylinder and the one or more inner cylinders are described with reference to a radius or diameter for the cylinder. In this discussion, a reference to a diameter corresponds to an inner diameter for a cylinder, and therefore describes the interior volume. To the degree that a cylinder does not correspond to a right circular cylinder, in some embodiments, the dimensions described herein can be used to represent the smallest right circular cylinder that can bound the actual interior shape of another type of cylinder.

In order to provide a sufficient amount of volume for water or another heat regulation fluid, the outer cylinder can have a diameter of about 16 cm to about 120 cm, for example about 16 cm to about 100 cm, about 20 cm to about 120 cm, or about 20 cm to about 100 cm. The height of the cylinder can be from about 30 cm to about 200 cm or more. Still larger outer cylinders can also be acceptable, but practical considerations such as the footprint of the photobioreactor can make diameters as described above more desirable in some embodiments.

An inner cylinder can have a smaller diameter and optionally a smaller length relative to the outer cylinder. Because water (and/or another heat regulation medium) can be substantially transparent to visible light, the water in the outer cylinder can cause only a minor attenuation/refraction of the visible light. However, the absorbance by algae in an inner cylinder can cause substantial attenuation if the thickness of the growth medium is too large. An inner cylinder diameter of about 3 cm to about 25 cm (for example about 3 cm to about 20 cm, about 5 cm to about 25 cm, or about 5 cm to about 20 cm) can be suitable for growth of algal microorganisms. The height of an inner cylinder can be any convenient height relative to the height of the outer cylinder.

In order to provide sufficient volume of water for heat regulation, the diameter of the outer cylinder can also be sufficiently larger than the diameter of an inner cylinder. In various aspects, a ratio of the diameter of the outer cylinder to an inner cylinder can be at least about 2.0, for example at least about 2.5 or at least about 3.0, and optionally up to about 6.0 or more. Still larger ratios can also be suitable, but practical considerations such as overall photobioreactor footprint relative to the volume for growing algae can lead to selection of ratios as described above in some embodiments. In the event that multiple inner cylinders are present, an effective diameter for all of the inner cylinders contained within an outer cylinder can be determined. The effective diameter for a plurality of inner cylinders can be determined by first calculating a total volume for the inner cylinders. An average height for the inner cylinders can then be used to determine a diameter that corresponds to the total volume of the inner cylinders. When a plurality of inner cylinders are present, the ratio of the diameter of the outer cylinder to an inner cylinder can be calculated based on an individual inner cylinder and/or based on the effective diameter of the plurality of inner cylinders, or the ratio can be determined for both the individual inner cylinders and the plurality of inner cylinders.

Additionally or alternately, the relative sizes of the outer cylinder and inner cylinder(s) can be characterized based on the surface areas of the respective cylinders. In such aspects, the ratio of the outer cylinder surface area to the inner cylinder(s) surface area can be at least about 4, for example at least about 8, at least about 12, or at least about 15, and optionally up to about 30 or more.

The outer cylinder and inner cylinder(s) can be formed from any convenient material substantially transparent to visible light. Typical materials with high transparency for visible light, such as glass, polymethylmethacrylate, or other various types of plastics, can also tend to be rather transparent to infrared radiation. Although infrared radiation is not typically utilized in photosynthesis, it can be absorbed by aqueous-based growth media. Since more than 50% of the radiant energy in sunlight can correspond to infrared radiation, the energy introduced into the growth medium by absorption of infrared radiation can lead to substantial temperature increases in a photobioreactor.

In order to reduce and/or minimize temperature increase due to absorbed infrared radiation, the inner surface and/or the outer surface of the outer cylinder can include material that blocks, inhibits, and/or reflects transmission of infrared radiation. A variety of commercial materials are available having substantially greater transparency in the visible range relative to transparency in the infrared range. Suitable materials can have a transmittance of at least about 0.6, for example at least about 0.7 or at least about 0.8, in the wavelength range of about 400 nm to about 700 nm. Additionally or alternately, suitable materials can have a transmittance of about 0.6 or less, for example about 0.5 or less or about 0.4 or less, for at least some wavelengths in the infrared range. The at least some wavelengths of the infrared range having the transmittance of about 0.6 or less (e.g., about 0.5 or less or about 0.4 or less) through the blocking, inhibiting, and/or reflecting material can correspond to wavelengths from about 800 nm to about 1100 nm, for example from about 850 nm to about 1100 nm, from about 900 nm to about 1100 nm, or from about 950 nm to about 1100 nm. It is noted that an IR coating on an inner surface and/or an outer surface of the outer cylinder can optionally but preferably provide an additional advantage by retaining infrared radiation emitted by the fluids in the cylinder(s) during night time or other periods when the photobioreactor is not exposed to light. This can assist with maintaining a stable temperature during periods where light is not impinging on the photobioreactor.

Use of a blocking, inhibiting, and/or reflective layer or coating on a surface of the outer cylinder (such as an outer surface) can provide advantages relative to using an adsorptive dye in the liquid media inside the outer cylinder. An absorptive dye can reduce and/or minimize the amount of infrared radiation reaching the inner cylinder. However, the absorption by such a dye in the outer cylinder can still lead to increases in the temperature of the media in the outer cylinder. Such temperature increases can reduce the moderating effect of having an inner cylinder within the media in the outer cylinder.

FIG. 1 shows an example of a tube-in-tube configuration for a photobioreactor. In FIG. 1, a photobioreactor 100 can include an outer cylinder 110 and an inner cylinder 140. The volume of outer cylinder 110 can contain a heat regulation fluid 112, such as water or another suitable fluid. In many aspects, the heat regulation fluid 112 can be a liquid, as liquids can tend to have greater heat capacities than gases. One or more outer cylinder inlets 121 can be used to introduce additional heat regulation fluid (whether water or another) into the volume of outer cylinder 110, while one or more outer cylinder outlets 123 can remove heat regulation fluid. The circulation or exchange of heat regulation fluid into and out of outer cylinder 110 can be used for active temperature control, for cleaning of the fluid in the cylinder, and/or for any other convenient purpose. In some aspects, an outer surface 130 of outer cylinder 110 can include a reflective coating or layer selective for reflection of infrared radiation relative to visible radiation. The inner cylinder 140 can similarly have inlets (not shown) and outlets (not shown).

Figure 2:
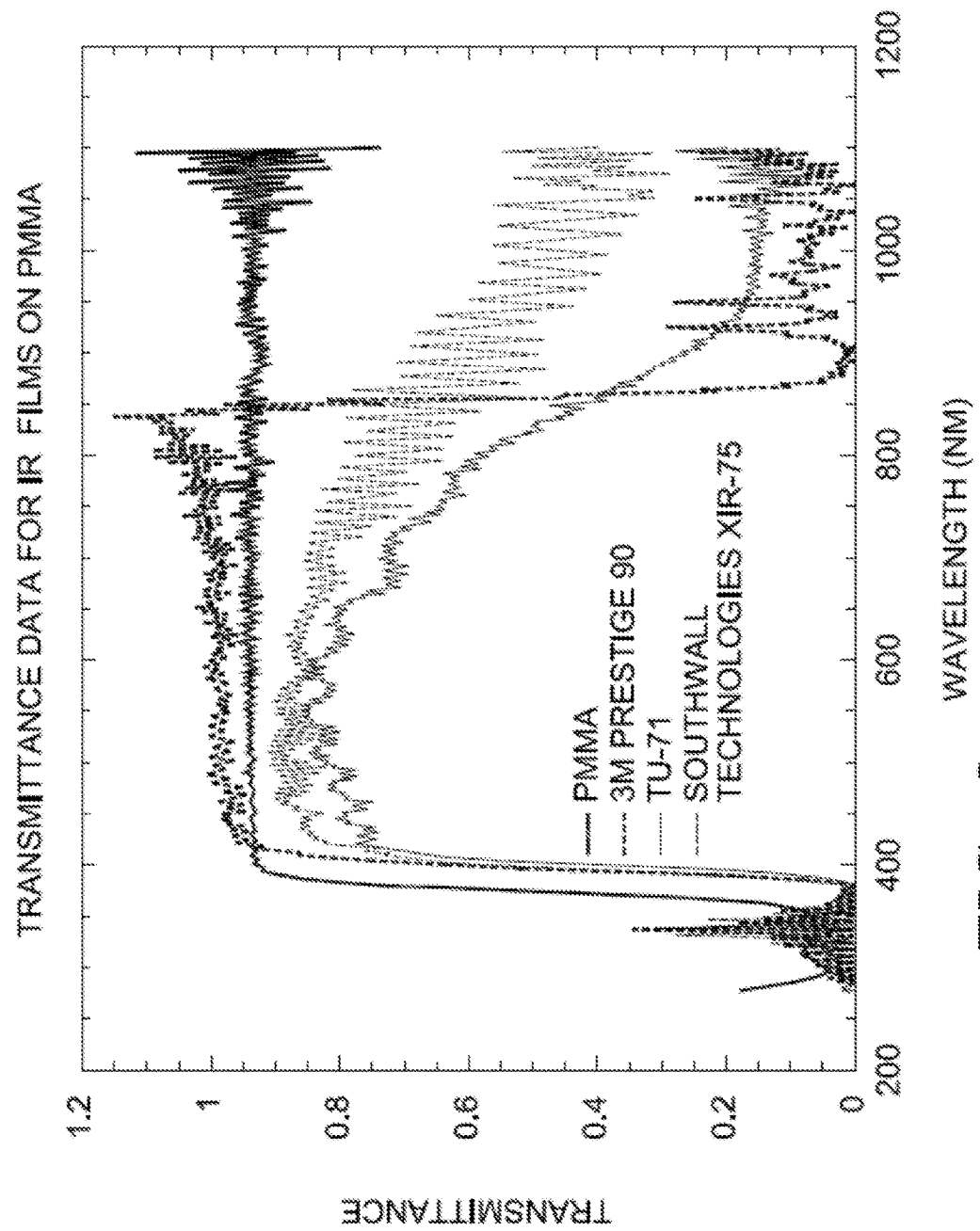
FIG. 2 shows examples of transmittance spectra for various coatings.

FIG. 2 shows an example of the transmittance at various wavelengths for several types of coatings or layers that can be suitable for coating an outer surface of an outer cylinder of a tube-in-tube photobioreactor. For the materials shown in FIG. 2, the transmittance for visible wavelengths of light is relatively high while the transmittance for infrared radiation is reduced. The data shown in FIG. 2 correspond to films of several commercially available products on top of a PMMA surface. The commercially available products correspond to a Prestige 90™ coating, available from 3M; a Refle-Shine TU-71™ coating, available from Tokai Rubber Industries, Ltd.; and an XIR-75™ coating available from Southwall Technologies. For comparison, the transmittance of the PMMA without an additional outer coating is also shown.

As shown in FIG. 2, the PMMA without a coating provides a relatively constant transmittance in both the visible and the infrared portions of the spectrum. This is in contrast to the PMMA surfaces that include the various reflective coatings. The Prestige 90™ coating provides the sharpest profile, as the transmittance in the visible region (~400-700 nm) is similar to PMMA without a coating, while the transmittance at about 850 nm or greater is about 0.2 or less with an average transmittance in the ~850-1100 nm region of about 0.1 or less. Although the other two coatings shown in FIG. 2 have a more gradual reduction in transmittance as wavelength increases, the TU-71™ coating and XIR75™ coating could additionally or alternately be suitable for use as a reflective coating. For example, the XIR75™ coating appears to have an average transmittance of less than about 0.6 in the wavelength range of about 950 nm to about 1100 nm, while the IR90™ coating appears to have an average transmittance of less than about 0.4 in the wavelength range of about 850 nm to 1100 about nm.

Figure 3:
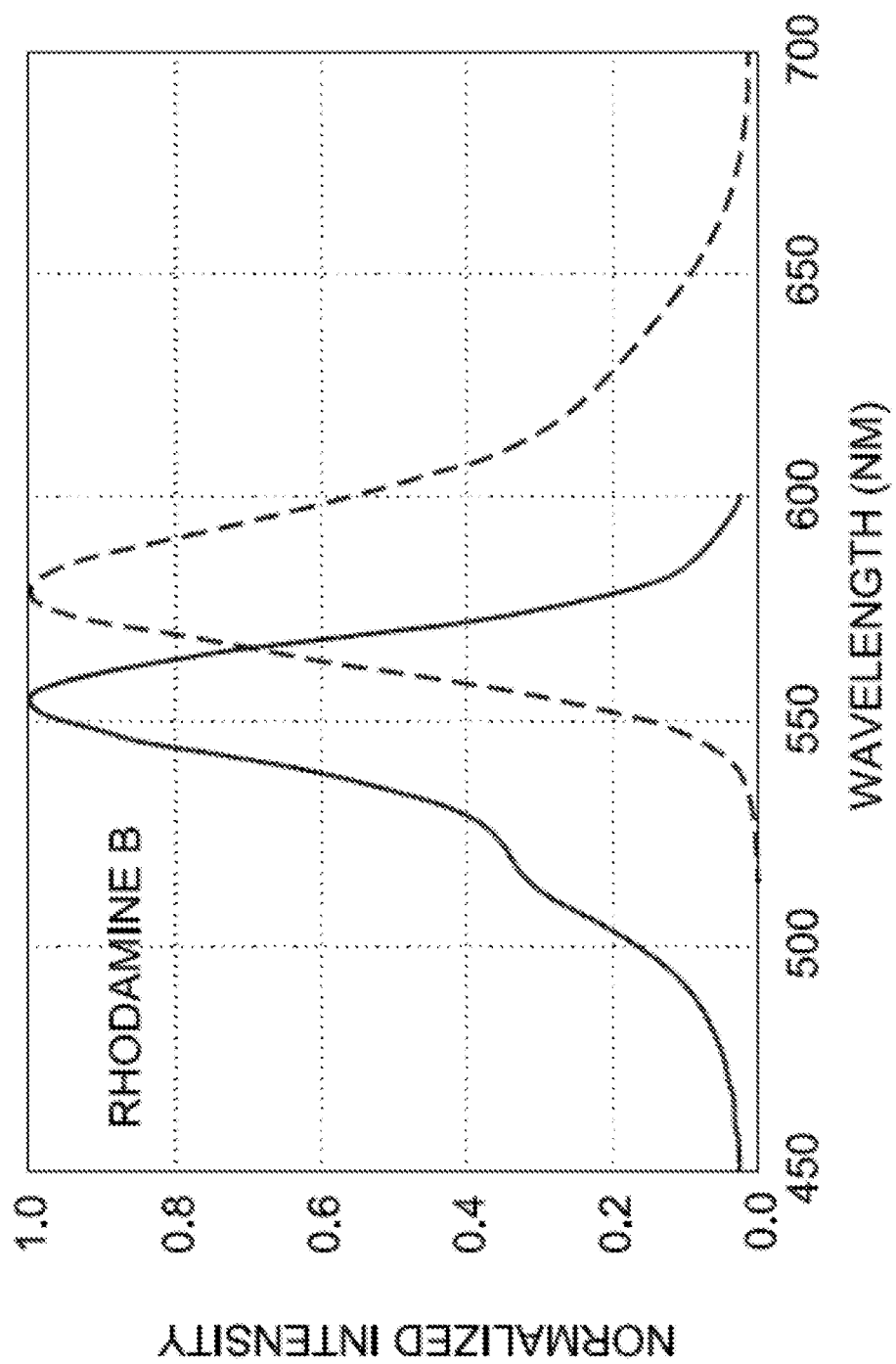
FIG. 3 shows an example of absorption and emission spectra for Rhodamine™ B.

It is noted that use of an outer reflective coating for the outer cylinder can be directly in contrast to prior photobioreactors that used dyes or chromophores in a fluid near/surrounding algae growth media. Conventional uses of dyes and/or chromophores can typically be related to attempting to regulate photosynthesis/the visible light spectrum, as opposed to heat/the infrared portion of the spectrum. FIG. 3 shows the absorbance and emission profile of Rhodamine™ B dye. As shown in FIG. 3, Rhodamine™ B appears to have a strong absorbance that peaks near ~550 nm and an emission spectrum that peaks near ~600 nm. Additionally, both the absorbance and the emission spectra appear to have low values in the region above ~800 nm. Based on the spectrum in FIG. 3, the use of Rhodamine™ B can serve primarily as a modifier of the visible light impinging on a growth medium (or, more to the point, on photosynthetic microorganisms contained therein). This is unrelated to the infrared reflection that can be achieved with an outer layer coating.

Figure 4:
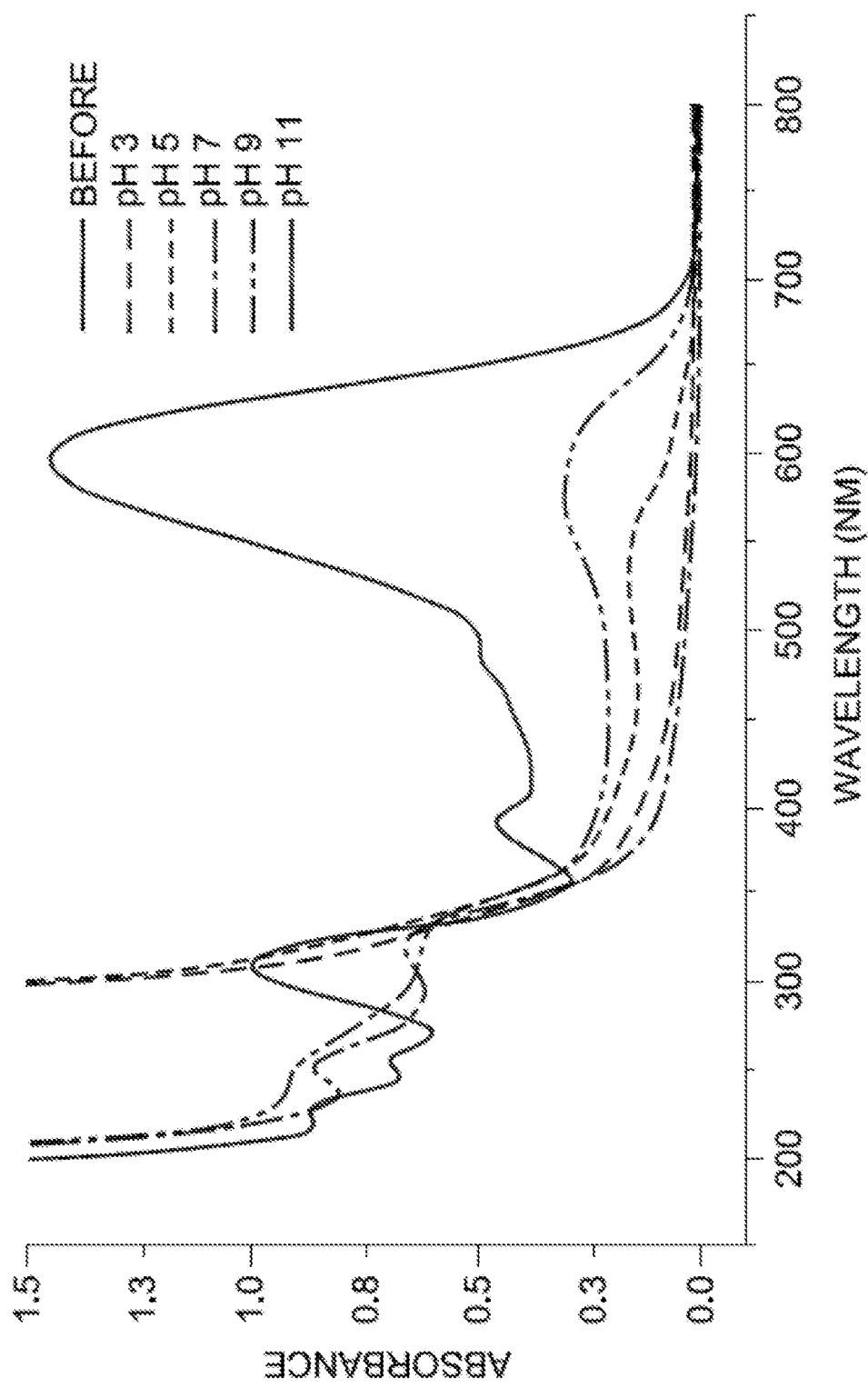
FIG. 4 shows examples of absorption spectra for a dichromate dye.

FIG. 4 shows an example of absorbance spectra for a dichromate dye at various pH values. As shown in FIG. 4, modifying the pH of a fluid containing a dichromate dye can allow for modification of the amount of visible light that passes through the fluid. By contrast, the absorbance for the dichromate dye at all pH values is relatively low in the region above ~800 nm, indicating little or no impact on the amount of infrared radiation that would reach growth media in an inner cylinder.

Active and Passive Operation

In various aspects, algae (photosynthetic microorganism) growth can be performed in the inner cylinder(s) of a tube-in-tube photobioreactor system. One of the factors that can substantially impact the growth of algae within the inner cylinder(s) can be the temperature in the inner cylinder. For a typical photobioreactor, the combination of impinging radiation and ambient temperature changes can result in changes in the temperature in the photobioreactor growth media of up to 20° C. or more during daytime versus nighttime hours.

One method for controlling the temperature of growth media can be to have a barrier layer and/or other temperature moderation layer of fluid. For example, a flat panel photobioreactor can have two separate fluid chambers. A first chamber can contain water and/or another fluid for adsorbing infrared radiation, while allowing the desirable visible radiation to pass through to the growth media/algae. However, such an arrangement can require active rotation of the panel photobioreactors in order to maintain a desired orientation relative to the position of the sun.

Instead of using a panel to form a protective layer, a tube-in-tube design can allow a barrier layer of water and/or another fluid to be used in an outer cylinder to moderate the temperature of the growth media in the inner cylinder(s). Because of the isotropic nature of a cylinder design, the orientation of the tube-in-tube photobioreactor can be appropriate regardless of the position of a light source. Thus, separate equipment for moving the photobioreactor to maintain a desired orientation can be avoided.

In some aspects, the water and/or other media in the outer cylinder can be circulated to exchange the water in the outer cylinder. This can be referred to as active temperature control. The media in the outer cylinder can be circulated so that water (and/or other media) at a first temperature can be replaced with water (and/or other media) at a second temperature. Thus, circulation can allow for heating and/or cooling of the media in the outer cylinder, depending on the desired temperature for the outer cylinder media. Any convenient type of circulation can be used. For example, a constant flow of media into (and therefore out of) the outer cylinder can be maintained, and/or a portion (up to all) of the media can be exchanged periodically.

Alternatively, in aspects where a layer for reflecting infrared radiation is used, the media in the outer cylinder can provide sufficient temperature control for the growth media in the inner cylinder(s) by passive temperature regulation. For passive temperature regulation, the heat regulation media in the outer cylinder is not exchanged and/or circulated on a schedule that is related to temperature swings external to the tube-in-tube photobioreactor. Instead, the heat regulation fluid in the outer cylinder can provide sufficient thermal mass so that any infrared radiation absorbed in the outer cylinder media can have only a reduced/minimized impact on the temperature of the growth media in the inner cylinder.

Using either active or passive temperature control, the temperature of the growth media in the inner cylinder can be maintained to within an inner cylinder tolerance of a growth temperature. The inner cylinder tolerance can be about 7° C. or less, for example about 5° C. or less, about 3° C. or less, about 2° C. or less, about 1° C. or less, or about 0.5° C. or less. When sunlight is the source of visible radiation for the photobioreactor, the inner cylinder tolerance can represent a maximum differential around an average daily temperature for the inner cylinder growth media over the course of a growth period, such as a growth period of about 3 days to about 30 days, for example about 5 days to about 15 days or about 5 days to about 10 days. For the above, the "average daily temperature" reflects the 24 hour cycle that is a characteristic time period associated with sunlight. When the light source other than sunlight is used, the inner cylinder tolerance can represent a maximum differential relative to the average temperature for a characteristic time period for the light source. Other characteristic time periods can include, but are not limited to, time periods of about 10 hours to about 100 hours. In some embodiments, the characteristic time period (if different from a daily cycle), can be at least about 10 hours, e.g., at least about 20 hours, at least about 30 hours, at least about 40 hours, at least about 50 hours, at least about 60 hours, at least about 70 hours, at least about 80 hours, or at least about 90 hours. Additionally or alternately, the characteristic time period (if different from a daily cycle) can be about 100 hours or less, for example 90 hours or less, 80 hours or less, 70 hours or less, 60 hours or less, 50 hours or less, 40 hours or less, 30 hours or less, or 20 hours or less. It is noted that each of the above lower limits for the characteristic time period is expressly contemplated in combination with each of the above upper limits.

The average temperature for the (growth) media in the inner cylinder can be between about 0° C. to about 60° C. For example, the average temperature for the media in the inner cylinder can be between about 0° C. and about 55° C., such as about 0° C. and about 50° C., about 0° C. and about 45° C., about 0° C. and about 40° C., about 0° C. and about 35° C., about 0° C. and about 30° C., about 0° C. and about 25° C., about 0° C. and about 20° C., about 0° C. and about 15° C., about 0° C. and about 10° C., about 5° C. and about 60° C., about 5° C. and about 55° C., about 5° C. and about 50° C., about 5° C. and about 45° C., about 5° C. and about 40° C., about 5° C. and about 35° C., about 5° C. and about 30° C., about 5° C. and about 25° C., about 5° C. and about 20° C., about 5° C. and about 15° C., about 5° C. and about 10° C., about 10° C. and about 60° C., about 10° C. and about 55° C., about 10° C. and about 50° C., about 10° C. and about 45° C., about 10° C. and about 40° C., about 10° C. and about 35° C., about 10° C. and about 30° C., about 10° C. and about 25° C., about 10° C. and about 20° C., about 10° C. and about 15° C., about 15° C. and about 60° C., about 15° C. and about 55° C., about 15° C. and about 50° C., about 15° C. and about 45° C., about 15° C. and about 40° C., about 15° C. and about 35° C., about 15° C. and about 30° C., about 15° C. and about 25° C., about 15° C. and about 20° C., about 20° C. and about 60° C., about 20° C. and about 55° C., about 20° C. and about 50° C., about 20° C. and about 45° C., about 20° C. and about 40° C., about 20° C. and about 35° C., about 20° C. and about 30° C., about 20° C. and about 25° C., about 25° C. and about 60° C., about 25° C. and about 55° C., about 25° C. and about 50° C., about 25° C. and about 45° C., about 25° C. and about 40° C., about 25° C. and about 35° C., about 25° C. and about 30° C., about 30° C. and about 60° C., about 30° C. and about 55° C., about 30° C. and about 50° C., about 30° C. and about 45° C., about 30° C. and about 40° C., or about 30° C. and about 35° C., about 35° C. and about 60° C., about 35° C. and about 55° C., about 35° C. and about 50° C., about 35° C. and about 45° C., about 35° C. and about 40° C., about 40° C. and about 60° C., about 40° C. and about 55° C., about 40° C. and about 50° C., about 40° C. and about 45° C., about 45° C. and about 60° C., about 45° C. and about 55° C., about 45° C. and about 50° C., about 50° C. and about 60° C., about 50° C. and about 55° C., or about 55° C. and about 60° C. As an example, an inner cylinder tolerance of 2° C. or less with an average daily temperature of 16° C. can correspond to having inner cylinder temperatures between 14° C. and 18° C. during a 24 hour period. It is noted that the average temperature for a characteristic time period, such as an average daily temperature, can vary due to seasonal ambient temperature variations.

The temperature of the media in the outer cylinder can also remain within an outer cylinder tolerance of an average temperature. The outer cylinder tolerance can be about 7° C. or less, for example about 5° C. or less, about 3° C. or less, about 2° C. or less, about 1° C. or less, or about 0.5° C. or less. The average temperature for the media in outer cylinder can be between about 0° C. and about 60° C. For example, the average temperature for the media in the outer cylinder can be between about 0° C. and about 55° C., such as about 0° C. and about 50° C., about 0° C. and about 45° C., about 0° C. and about 40° C., about 0° C. and about 35° C., about 0° C. and about 30° C., about 0° C. and about 25° C., about 0° C. and about 20° C., about 0° C. and about 15° C., about 0° C. and about 10° C., about 5° C. and about 60° C., about 5° C. and about 55° C., about 5° C. and about 50° C., about 5° C. and about 45° C., about 5° C. and about 40° C., about 5° C. and about 35° C., about 5° C. and about 30° C., about 5° C. and about 25° C., about 5° C. and about 20° C., about 5° C. and about 15° C., about 5° C. and about 10° C., about 10° C. and about 60° C., about 10° C. and about 55° C., about 10° C. and about 50° C., about 10° C. and about 45° C., about 10° C. and about 40° C., about 10° C. and about 35° C., about 10° C. and about 30° C., about 10° C. and about 25° C., about 10° C. and about 20° C., about 10° C. and about 15° C., about 15° C. and about 60° C., about 15° C. and about 55° C., about 15° C. and about 50° C., about 15° C. and about 45° C., about 15° C. and about 40° C., about 15° C. and about 35° C., about 15° C. and about 30° C., about 15° C. and about 25° C., about 15° C. and about 20° C., about 20° C. and about 60° C., about 20° C. and about 55° C., about 20° C. and about 50° C., about 20° C. and about 45° C., about 20° C. and about 40° C., about 20° C. and about 35° C., about 20° C. and about 30° C., about 20° C. and about 25° C., about 25° C. and about 60° C., about 25° C. and about 55° C., about 25° C. and about 50° C., about 25° C. and about 45° C., about 25° C. and about 40° C., about 25° C. and about 35° C., about 25° C. and about 30° C., about 30° C. and about 60° C., about 30° C. and about 55° C., about 30° C. and about 50° C., about 30° C. and about 45° C., about 30° C. and about 40° C., about 30° C. and about 35° C., about 35° C. and about 60° C., about 35° C. and about 55° C., about 35° C. and about 50° C., about 35° C. and about 45° C., about 35° C. and about 40° C., about 40° C. and about 60° C., about 40° C. and about 55° C., about 40° C. and about 50° C., about 40° C. and about 45° C., about 45° C. and about 60° C., about 45° C. and about 55° C., about 45° C. and about 50° C., about 50° C. and about 60° C., about 50° C. and about 55° C., or about 55° C. and about 60° C.

Algae Feedstock

Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

In the discussion herein, a feed derived from a biological source (i.e., a biocomponent feed(stock)) refers to a feedstock derived from a biological raw material component, such as vegetable fats/oils or animal fats/oils, fish oils, pyrolysis oils, and algae lipids/oils, as well as components of such materials. In particular, a feed derived from a biological source can be a feed of algae in an aqueous environment, such as an algae culture or other feed containing algae in water.

Major classes of lipids can include, but are not necessarily limited to, fatty acids, glycerol-derived lipids (including fats, oils and phospholipids), sphingosine-derived lipids (including ceramides, cerebrosides, gangliosides, and sphingomyelins), steroids and their derivatives, terpenes and their derivatives, fat-soluble vitamins, certain aromatic compounds, and long-chain alcohols and waxes.

In living organisms, lipids generally serve as the basis for cell membranes and as a form of fuel storage. Lipids can also be found conjugated with proteins or carbohydrates, such as in the form of lipoproteins and lipopolysaccharides.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 40 wt %, of lipids based on total weight of the biomass itself.

Operating Conditions—Algae Growth

In various aspects, the inner cylinder(s) of the tube-in-tube photobioreactor can contain growth media that includes photosynthetic microorganisms such as algae. The growth media can be any convenient growth media for growth of (photosynthetic) microorganisms. Typically the growth media can correspond to an aqueous media with a desired level of salinity. Algae (or other photosynthetic microorganisms) in the inner cylinder(s) can be exposed to sunlight and/or another light source operating based on an illumination profile for a period of time, such as a day, multiple days, or even months. As the algae grow, the concentration of algae in the growth vessel can increase. At some point, increased microorganism growth can result in reduced viability, due to crowding, reduced light access, reduced nutrient access, and the like, and combinations thereof. This can be addressed by periodically or continuously diluting the microorganism density in the growth vessel to maintain it within acceptable levels.

In addition to providing illumination, a variety of other types of input for the growth media in the inner cylinder(s) can be controlled either initially or during the growth process. Additional factors that can be relevant for algae growth can include, for instance, $CO_2$ concentration in the growth media; oxygen content in the growth media; pH of the growth media; presence of other nutrients, such as nitrogen or phosphorus in the growth media; and/or other factors.

In some aspects, the source of $CO_2$ (abbreviated as $CO_2$) can be the primary acidic component in the growth media, and therefore the pH can be controlled by controlling $CO_2$ content. Optionally, $CO_2$ can be introduced into the volume of the inner cylinder(s) via an inlet (e.g., that allows for bubbling $CO_2$ into the vessel). Additionally or alternatively, an aeration port can be used to introduce $CO_2$. A corresponding outlet can allow for removal of excess $CO_2$ from the inner cylinder. Another additional or alternative option can be to circulate growth media through the inner cylinder, with exchange of gases such as $CO_2$ being performed while the growth media is outside of the inner cylinder volume. It is noted that the inlet(s) and outlet(s) for the inner cylinder (or plurality of inner cylinders) can allow for introduction and removal of fluids from the inner cylinder without providing fluid communication with the heat regulation fluid in the outer cylinder. A flow meter or another convenient device can be used to control the input flow rate of $CO_2$ into the inner cylinder(s). In some aspects, during exposure of algae to sunlight and/or another light source, it may be desirable to hold the $CO_2$ concentration at a an appropriate (and optionally a relatively constant) value.

In some aspects, the oxygen content in the growth media can be controlled. Algae can produce molecular oxygen as a by-product of photosynthesis, and removal of oxygen to control the concentration can be beneficial for algae growth. As noted above for $CO_2$, the $O_2$ concentration can be managed based on removing $O_2$ from the inner cylinder volume via ports and/or processing the growth media to remove $O_2$ while the growth media is outside of the inner cylinder.

In addition to inputs and outputs for the growth media, the inner cylinder(s) can also include features to allow for movement of water and/or growth media within the inner cylinders. Introducing movement or turbulence into growth media for algae can be beneficial for maintaining a similar growth environment for the algae and/or other micro-organisms in the growth media. One option can be to include a mechanical agitator in the inner cylinder, to increase mixing within the vessel. Additionally or alternately, a sparging mechanism can be used to provide movement or agitation of the water/growth medium in the growth vessel. As an example, a sparging mechanism could be used for introduction of $CO_2$ into the growth vessel.

ADDITIONAL EMBODIMENTS

Embodiment 1

A method for growing micro-organisms, comprising: providing a first cylinder having a first volume containing a heat regulation fluid, a diameter of the first cylinder being about 15 cm to about 120 cm, the first cylinder having a surface comprising a coating, the coated surface having an average transmittance for wavelengths between about 400 nm and about 700 nm of at least about 0.6 and an average transmittance for wavelengths between about 950 nm and about 1100 nm of about 0.5 or less; providing a second cylinder having a second volume containing a growth media comprising micro-organisms, the second cylinder being contained within the first cylinder, a longest axis of the second cylinder being substantially parallel to a longest axis of the first cylinder, a diameter of the second cylinder being about 3 cm to about 25 cm, a ratio of a surface area of the first cylinder to a surface area of the second cylinder being at least about 4, for example at least about 8 or at least about 12; exposing the cylinder to a light source comprising visible radiation and infrared radiation to grow the micro-organisms; and maintaining an average temperature of the growth media within the second cylinder of about 0° C. to about 60° C. during a characteristic time period.

Embodiment 2

The method of Embodiment 1, wherein the characteristic time period is about 10 hours to about 100 hours, for example at least about 20 hours or at least about 40 hours and/or about 80 hours or less or about 60 hours or less.

Embodiment 3

The method of any of the above embodiments, wherein the average temperature of the growth media in the second cylinder during the characteristic time period is maintained using passive temperature regulation, the passive temperature regulation optionally comprising maintaining the average temperature without circulation of the heat regulation media based on an illumination schedule associated with the light source.

Embodiment 4

The method of any of the above embodiments, wherein the growth media in the second cylinder is exposed to the light source while the second cylinder is oriented in a substantially vertical direction.

Embodiment 5

The method of any of the above embodiments, wherein a second cylinder temperature tolerance relative to the average temperature of the growth media in the second cylinder during the characteristic time period is about 5° C. or less, for example about 3° C. or less, about 2° C. or less, about 1° C. or less, or about 0.5° C. or less.

Embodiment 6

The method of any of the above embodiments, wherein an outer cylinder temperature tolerance relative to an average temperature of the heat regulation fluid in the first cylinder during the characteristic time period is about 5° C. or less, for example about 3° C. or less, about 2° C. or less, about 1° C. or less, or about 0.5° C. or less.

Embodiment 7

The method of embodiment 1, wherein the method comprises providing a plurality of second cylinders having a plurality of second volumes containing a growth media comprising micro-organisms.

Embodiment 8

A system for growing micro-organisms, comprising: a first cylinder having a first volume, a diameter of the first cylinder being about 15 cm to about 120 cm, the first cylinder having a surface comprising a coating, the coated surface having an average transmittance for wavelengths between about 400 nm and about 700 nm of at least about 0.6 and an average transmittance for wavelengths between about 950 nm and about 1100 nm of about 0.5 or less; a second cylinder having a second volume, the second cylinder being contained within the first cylinder, a long axis of the second cylinder being substantially parallel to a long axis of the first cylinder, a diameter of the second cylinder being about 3 cm to about 25 cm, a ratio of a surface area of the first cylinder to a surface area of the second cylinder being at least about 4, for example at least about 8 or at least about 12; a first cylinder inlet and a first cylinder outlet in fluid communication with the first volume; and a second cylinder inlet and a second cylinder outlet in fluid communication with the second volume and not in fluid communication with the first volume.

Embodiment 9

The system of Embodiment 8, wherein the system comprises a plurality of second cylinders.

Embodiment 10

The method of Embodiment 7 or the system of Embodiment 9, wherein a ratio of the diameter of the first cylinder to a combined effective diameter of the plurality of second cylinders is at least about 2.0, and/or wherein a ratio of the diameter of the first cylinder to a diameter of each of the plurality of second cylinders is at least about 2.0.

Embodiment 11

The method or system of any of the above embodiments, wherein the coated surface comprises a coated outer surface and/or a coated inner surface.

Embodiment 12

The method or system of any of the above embodiments, wherein one or more of the following is satisfied: the average transmittance for wavelengths between about 400 nm and about 700 nm is at least about 0.7, for example at least about 0.8; the average transmittance for wavelengths between about 950 nm and about 1100 nm is about 0.4 or less, for example about 0.3 or less; and the average transmittance for wavelengths between about 400 nm and about 700 nm is at least about twice the average transmittance for wavelengths between about 950 nm and about 1100 nm.

Embodiment 13

The method or system of any of the above embodiments, wherein the coated surface has an average transmittance for wavelengths between about 900 nm and about 1100 nm, optionally between about 850 nm and about 1100 nm and/or between about 800 nm and about 1100 nm, of about 0.5 or less, for example about 0.4 or less or about 0.3 or less.

Embodiment 14

The method or system of any of the above embodiments, wherein a ratio of the diameter of the first cylinder to the diameter of the second cylinder is at least about 2.0, for example at least about 2.5 or at least about 3.0.

Embodiment 15

The method or system of any of Embodiments 1-6, 8, or 11-14, wherein the second cylinder is co-axial with the first cylinder.

Examples

Temperature Variations for Photobioreactors

FIGS. 5A-5D show results from modeling of the temperature inside various photobioreactor configurations. The modeled photobioreactors corresponded to algae bubble column photobioreactors. For configurations with a tube-in-tube photobioreactor, the photobioreactor had an inner cylinder that was concentric with the outer cylinder. The temperature of the photobioreactors was modeled based on the measured weather conditions in south Texas during a roughly two week period during either April or August. The measured weather conditions included ambient temperature, wind, and available solar radiation. For configurations including a reflective coating, the reflective coating was modeled as providing approximately 100% reflection of infrared wavelengths.

Figure 5A:
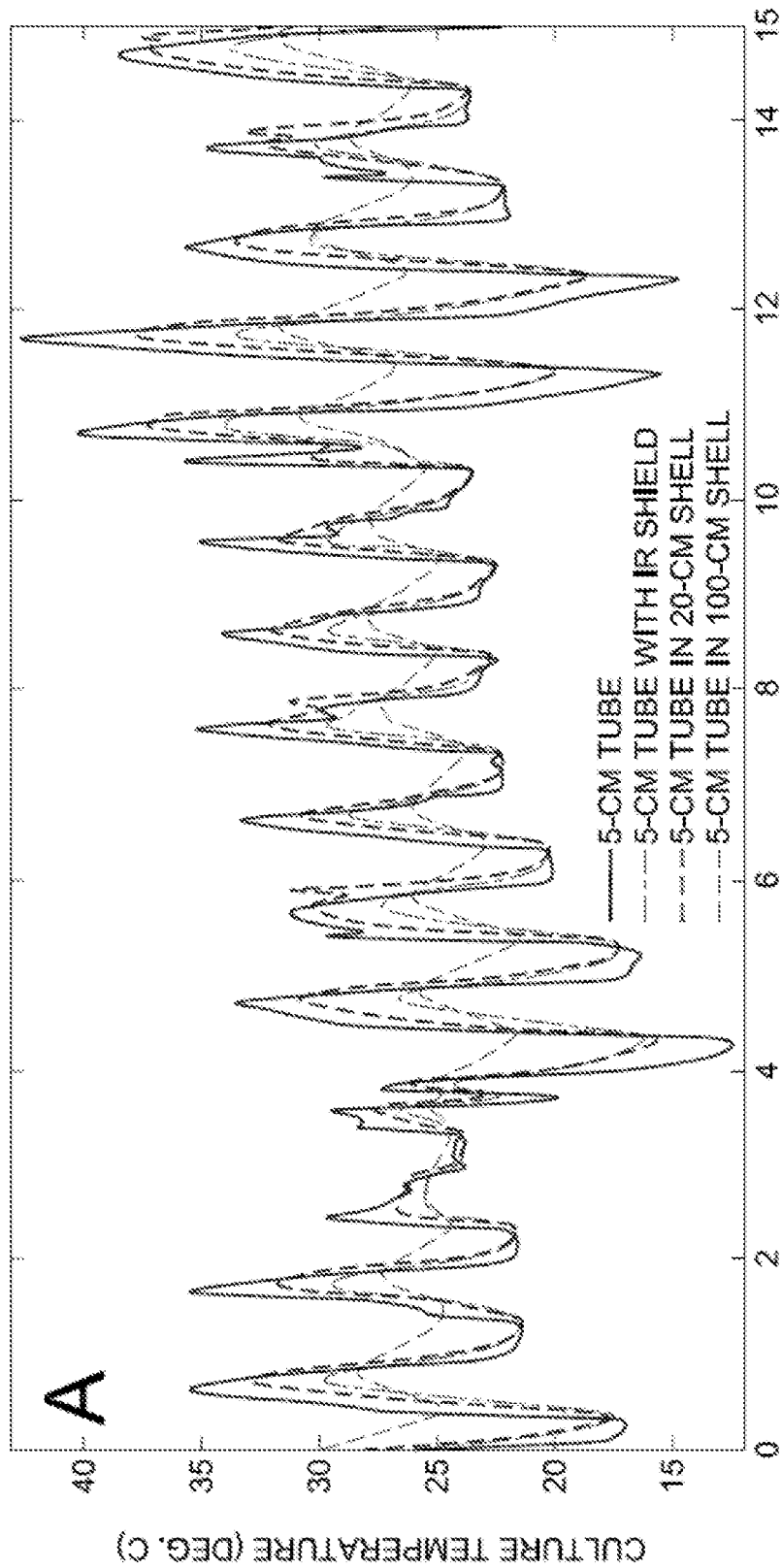
FIGS. 5A, 5B, 5C, and 5D show temperature values from monitoring of growth media in various photobioreactors over a period of time.

The modeled results in FIG. 5A correspond to cylinders containing growth media that had a ~5 cm diameter during exposure to the measured April conditions. The plots in FIG. 5A show the temperature variations for the growth media inside the cylinder for a configuration of a) the ~5 cm diameter cylinder, b) the ~5 cm diameter cylinder with an IR reflective coating, c) the ~5 cm diameter cylinder inside of a ~20 cm diameter outer cylinder that contained water, and d) the ~5 cm diameter cylinder inside of a ~100 cm diameter cylinder that contained water. As shown in the modeled results in FIG. 5A, the ~5 cm diameter tube alone appeared to have temperature variations in the growth media that ranged from less than 15° C. to greater than 40° C. Adding an IR reflective coating to the exterior of the ~5 cm diameter tube appeared to reduce the temperature variations, but the temperature still varied from about 20° C. to greater than about 30° C. In the modeled results, using a tube-in-tube configuration with a ~20 cm diameter outer tube appeared to result in similar temperature fluctuations to the ~5 cm diameter tube alone. Using a tube-in-tube configuration with a ~100 cm diameter outer tube appeared to have similar temperature fluctuations to using an IR coating on the ~5 cm tube. The results in FIG. 5A appear to demonstrate that use of an outer cylinder containing water (and/or another heat regulation fluid) by itself can still allow for large temperature swings for the temperature of growth media in an inner cylinder.

Figure 5B:
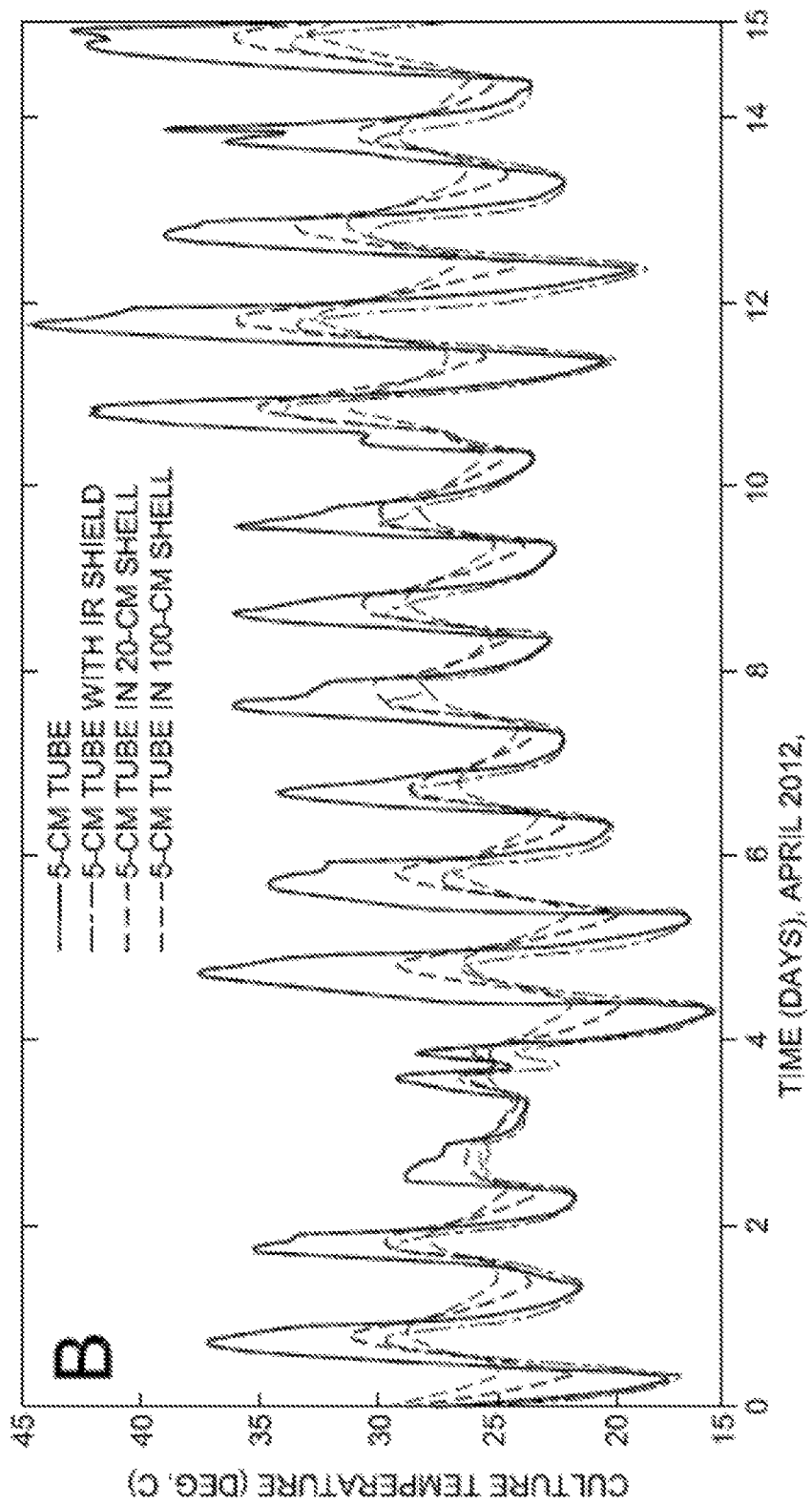
Figure 5C:
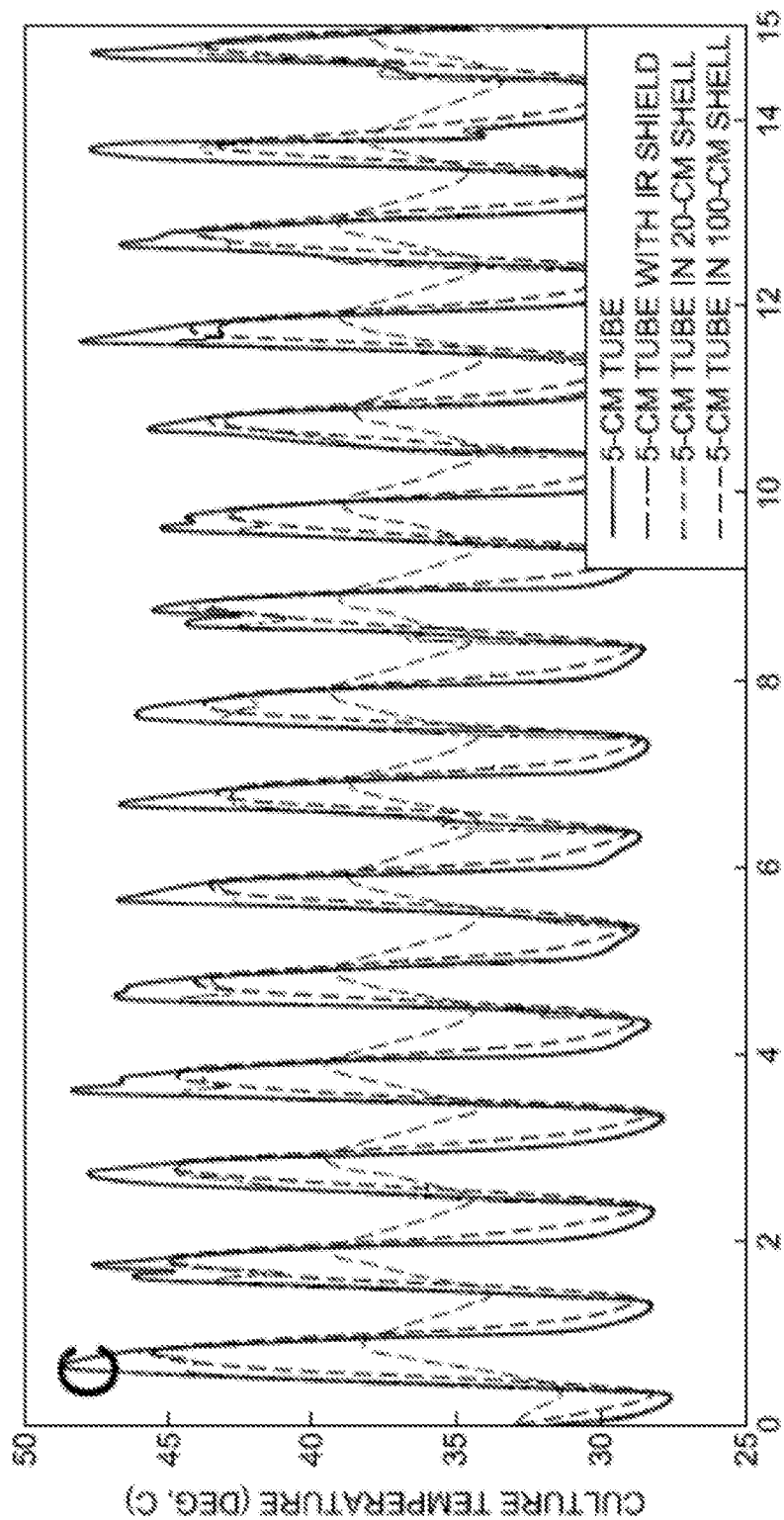

The temperature swings for growth media in an inner cylinder were more apparent in the modeled results shown in FIG. 5C. FIG. 5C shows results for configurations similar to FIG. 5A, but with ambient weather conditions that were measured during August. In FIG. 5C, the tube-in-tube configurations appeared to provide only a modest advantage relative to the temperature variations for the ~5 cm diameter tube alone. Use of an IR coating for the ~5 cm diameter tube reduced the temperature variations, but still appeared to allow for temperature variations from less than 35° C. to about 40° C.

Figure 5D:
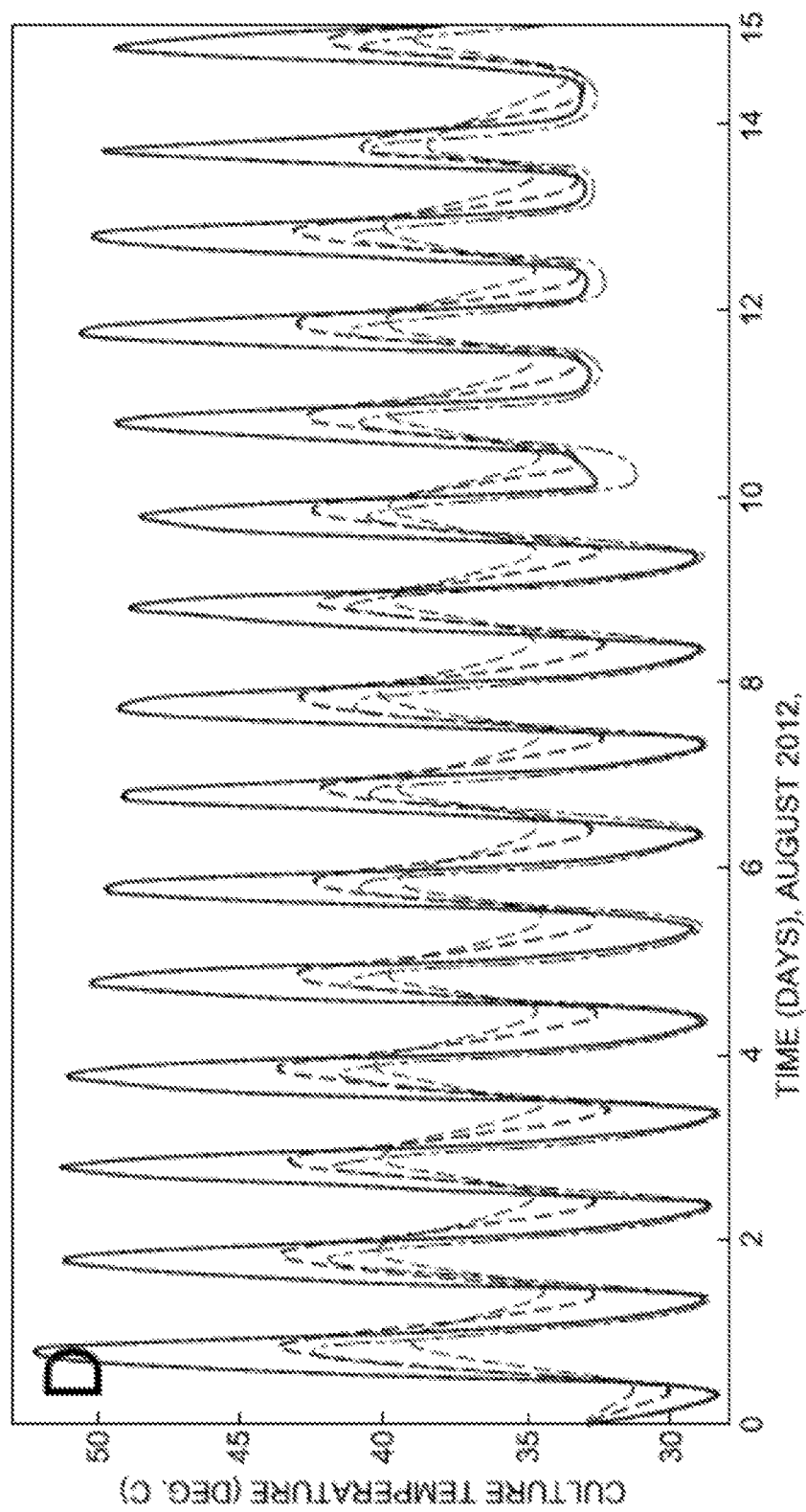

FIGS. 5B and 5D show results from modeling of ~20 cm diameter cylinders containing growth media, including results from a) a ~20 cm diameter cylinder, b) a 20 cm diameter cylinder with an IR reflective coating, c) a ~20 cm diameter cylinder in a ~50 cm diameter outer cylinder filled with water, and d) a ~20 cm diameter cylinder in a ~100 cm diameter cylinder filled with water. FIG. 5B corresponds to modeled temperatures based on the ambient weather conditions measured during April, while FIG. 5D corresponds to modeled temperatures based on the ambient weather conditions measured during August.

The results in FIGS. 5B and 5D are qualitatively similar to the results shown in FIGS. 5A and 5C, respectively. A comparison of the modeled results in FIGS. 5B and 5D relative to the modeled results in FIGS. 5A and 5C can appear to show that simply increasing the size of the vessel used for containing the growth media does not have a strong impact on the regulation of temperature in the growth media. Similarly, increasing the size of a vessel having an IR reflective coating, or increasing the size of an outer vessel for a tube-in-tube configuration did not appear to have a strong impact on the regulation of temperature in the growth media.

Figure 6A:
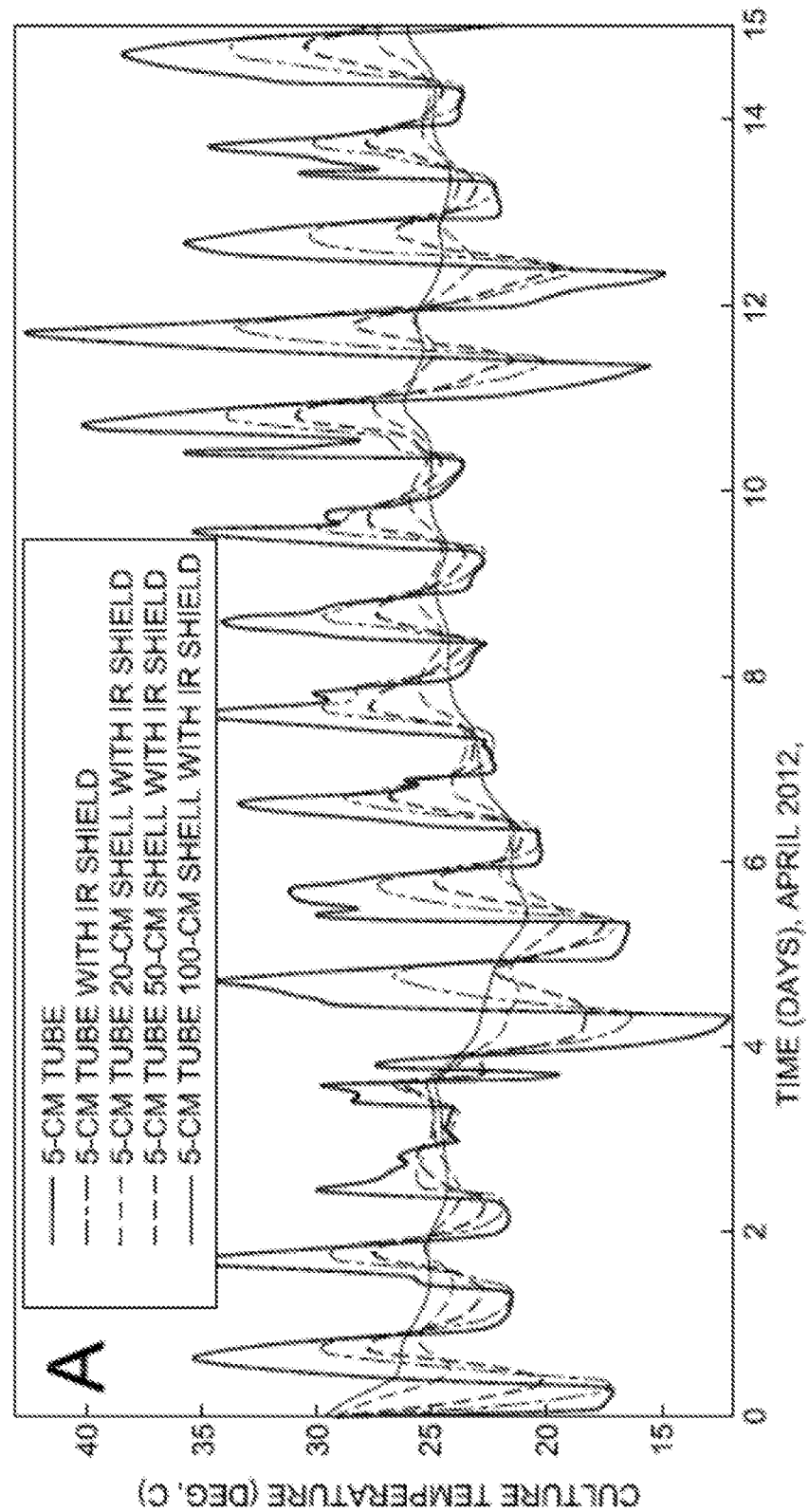
FIGS. 6A, 6B, 6C, and 6D show temperature values from monitoring of growth media in various photobioreactors over a period of time.
Figure 6B:
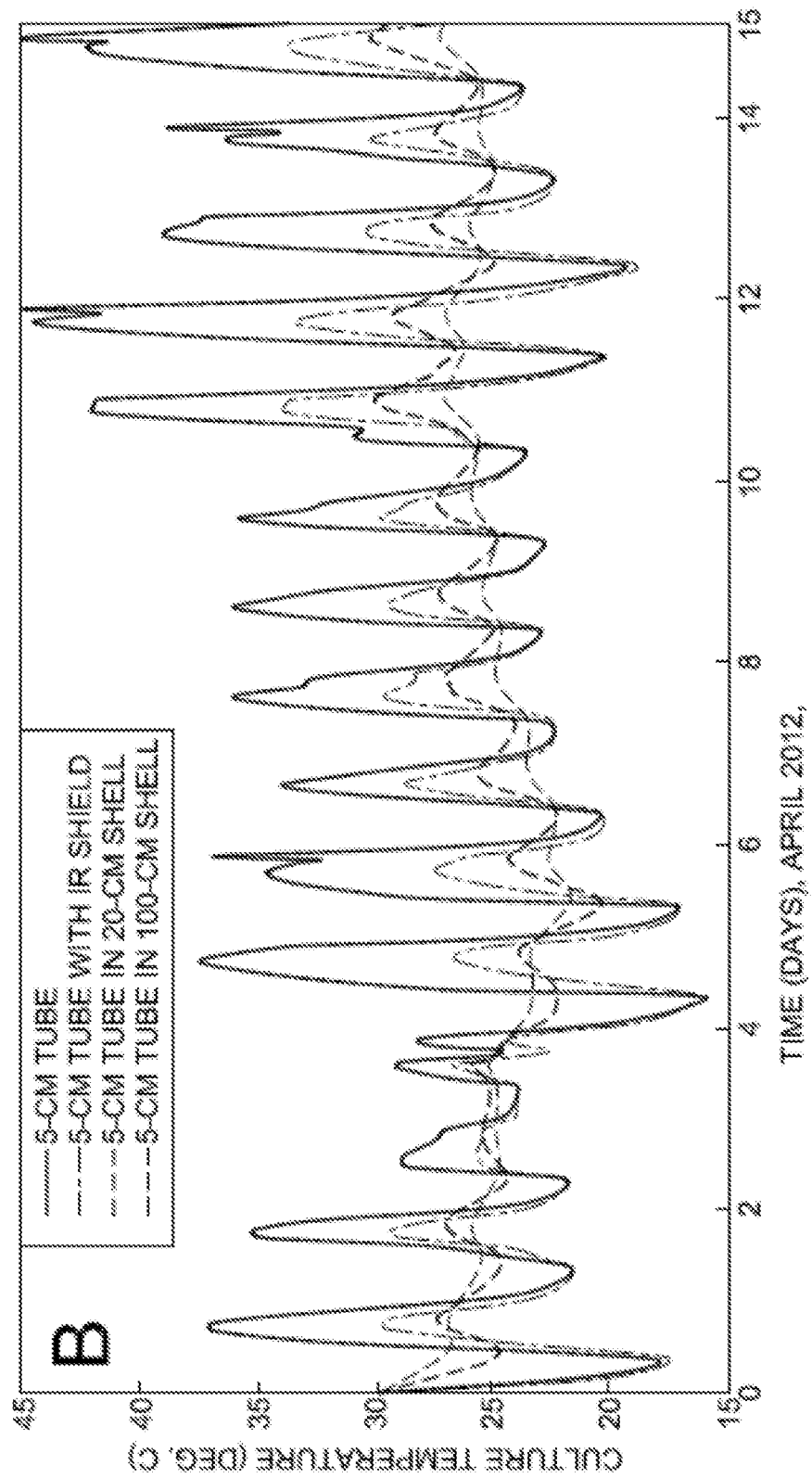
Figure 6C:
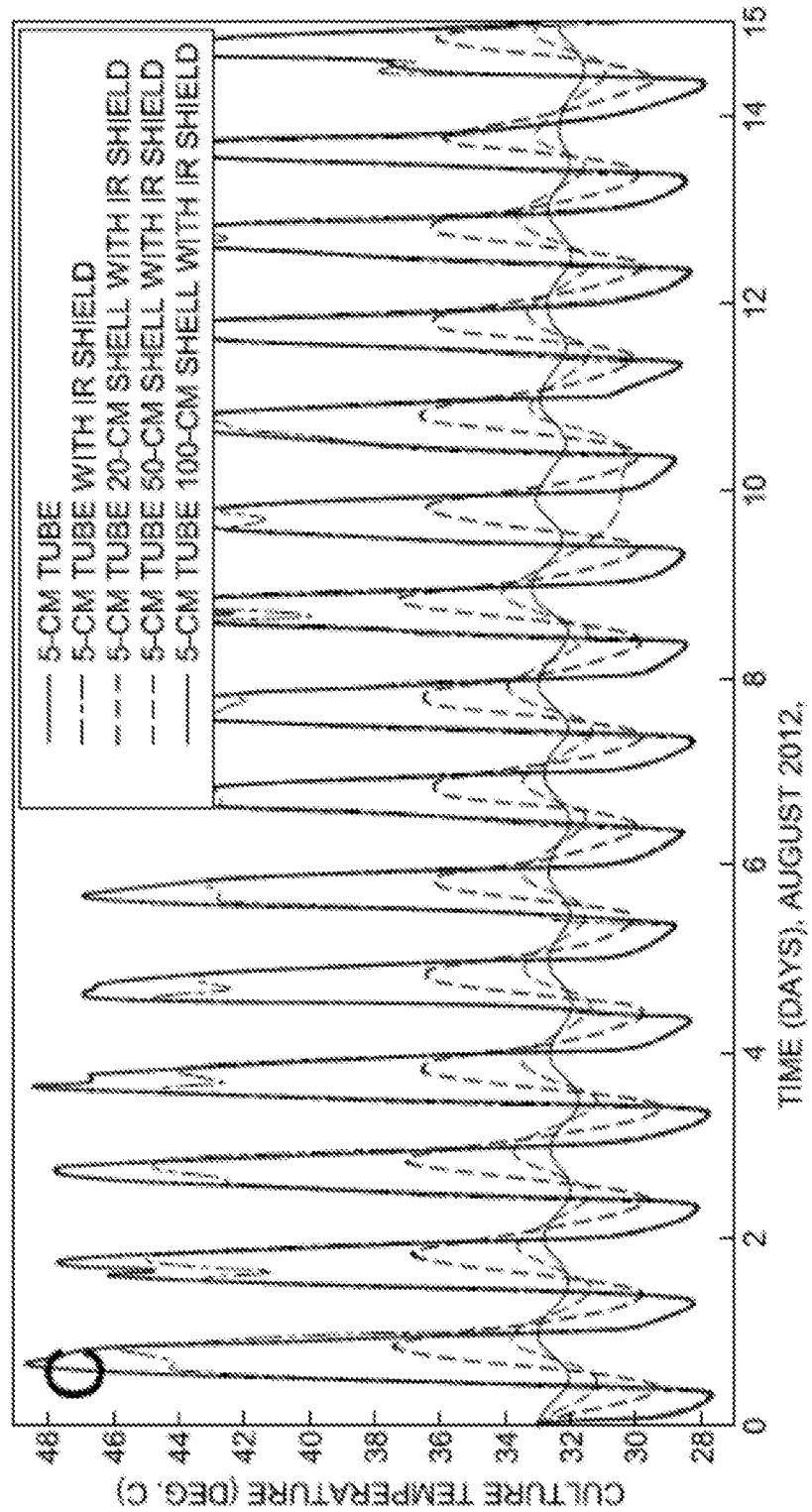
Figure 6D:
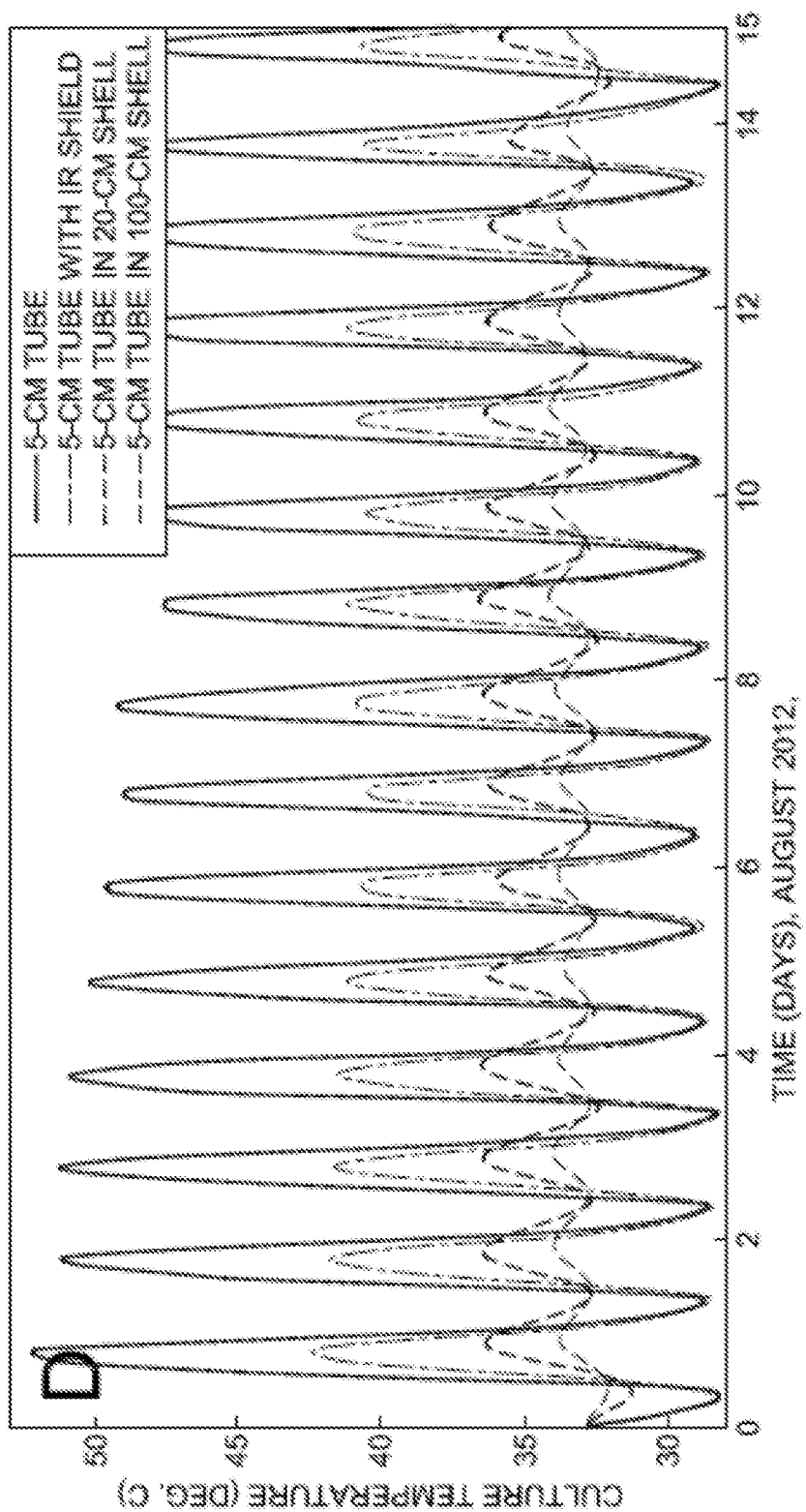

FIGS. 6A-6D show modeled results for the growth media temperature for cylinders having a tube-in-tube configuration with an IR reflective coating on an outer surface of the outer cylinder. Similar to FIGS. 5A-5D, the temperatures in 6A and 6C were modeled based on measured ambient weather conditions in April while the temperatures in 6B and 6D were modeled based on ambient weather conditions measured in August. FIGS. 6A and 6C show results for inner cylinders having a ~5 cm diameter with outer cylinders having ~20 cm, ~50 cm, and ~100 cm diameters. FIGS. 6B and 6D show results for inner cylinders having a ~20 cm diameter with outer cylinders having a ~50 cm diameter and a ~100 cm diameter. For comparison, the results from having only the "inner" cylinder with and without an IR coating are also shown in FIGS. 6A-6D.

As shown in FIGS. 6A-6D, use of an outer cylinder with an IR reflective coating appeared to reduce/minimize the temperature fluctuations for the growth media in an inner cylinder relative to having an inner cylinder alone (either with or without an IR reflective coating). In contrast to FIGS. 5A-5D, increasing the size of an outer cylinder having an IR reflective coating appeared to further reduce/minimize the temperature variations for growth media in an inner cylinder. This appears to show that use of an IR reflective coating can provide an unexpected synergy with use of an outer cylinder, as neither an IR reflective coating nor an outer cylinder alone demonstrated a size-related impact on temperature regulation.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method for growing micro-organisms, comprising:
   a) providing a first cylinder having a first volume containing a heat regulation fluid, a diameter of the first cylinder being 15 cm to about 120 cm, the first cylinder having a surface comprising a coating, the coated surface having an average transmittance for wavelengths between about 400 nm and about 700 nm of at least about 0.6 and an average transmittance for wavelengths between about 950 nm and about 1100 nm of about 0.5 or less;
   b) providing a second cylinder having a second volume containing a growth media comprising micro-organisms, the second cylinder being contained within the first cylinder, a longest axis of the second cylinder being substantially parallel to a longest axis of the first cylinder, a diameter of the second cylinder being about 3 cm to about 25 cm, a ratio of a surface area of the first cylinder to a surface area of the second cylinder being at least 4;
   c) exposing the cylinder to a light source comprising visible radiation and infrared radiation to grow the micro-organisms; and
   d) maintaining an average temperature of the growth medium within the second cylinder of about 0° C. to about 60° C. during a pre-selected time period.

2. The method of claim 1, wherein the pre-selected time period is about 10 hours to about 100 hours.

3. The method of claim 1, wherein the average transmittance for wavelengths between about 400 nm and about 700 nm is at least 0.7, and/or wherein the average transmittance for wavelengths between about 950 nm and about 1100 nm is 0.4 or less.

4. The method of claim 1, wherein a ratio of the diameter of the First cylinder to the diameter of the second cylinder is at least 2.0.

5. The method of claim 1, wherein the average temperature of the growth medium in the second cylinder during the pre-selected time period is maintained using passive temperature regulation.

6. The method of claim 5, wherein maintaining the average temperature of the growth medium in the second cylinder during the pre-selected time period using passive temperature regulation comprises maintaining the average temperature without circulation of the heat regulation medium based on an illumination schedule associated with the light source.

7. The method of claim 1, wherein the growth medium in the second cylinder is exposed to the light source while the second cylinder is oriented in a substantially vertical direction.

8. The method of claim 1, wherein a second cylinder temperature tolerance relative to the average temperature of the growth medium in the second cylinder during the pre-selected time period is 5° C. or less.

9. The method of claim 1, wherein an outer cylinder temperature tolerance relative to an average temperature of the heat regulation fluid in the first cylinder during the pre-selected time period is 5 or less.

10. The method of claim 1, wherein the method comprises providing a plurality of second cylinders having a plurality of second volumes containing a growth medium comprising micro-organisms.

11. The method of claim 10, wherein a ratio of the diameter of the first cylinder to a combined effective diameter of the plurality of second cylinders is at least 2.0, and/or wherein a ratio of the diameter of the first cylinder to a diameter of each of the plurality of second cylinders is at least 2.0.

* * * * *